United States Patent [19]
Annino et al.

[11] Patent Number: 5,116,764
[45] Date of Patent: May 26, 1992

[54] DUAL-COLUMN, DUAL-DETECTOR GAS DETECTOR AND ANALYZER

[76] Inventors: Raymond Annino, 9 Winchester Rd., North Smithfield, R.I. 02895; Michael L. Bartlett, 610 Elm St., Walpole, Mass. 02081; Edwin L. Karas, 475 Ware St., Mansfield, Mass. 02048; Dale E. Lueck, 19 Chestnut Hill Rd., Chelmsford, Mass. 01824; John L. Middleton, 4 Hudson Rd., Lexington, Mass. 02173; Richard Villalobos, 19 Trout Farm La., Duxbury, Mass. 02332

[21] Appl. No.: 224,505

[22] Filed: Jul. 26, 1988

[51] Int. Cl.$^5$ .......................................... G01N 30/02
[52] U.S. Cl. .................................... 436/161; 73/23.22; 73/23.35; 73/23.36; 324/464; 364/497; 422/54; 422/89; 422/97; 422/98
[58] Field of Search ................ 422/98, 54, 89, 97; 436/161, 151; 250/382, 384, 423 P, 423 R; 324/464; 73/23.4, 23.35, 23.36, 23.22; 364/498, 497

[56] References Cited

U.S. PATENT DOCUMENTS

| | | | |
|---|---|---|---|
| 2,959,677 | 11/1960 | Robinson et al. | 250/423 P X |
| 3,425,806 | 2/1969 | Karmen | 422/54 X |
| 3,443,415 | 5/1969 | Clardy | 73/23.22 |
| 3,961,248 | 6/1976 | Kawamura | 422/97 X |
| 4,309,898 | 1/1982 | Horton | 73/23.35 |
| 4,346,055 | 8/1982 | Murphy et al. | 422/54 |
| 4,387,359 | 7/1983 | Tien et al. | 422/98 X |
| 4,517,461 | 5/1985 | Crandall | 422/54 |
| 4,670,405 | 6/1987 | Stetter et al. | 422/98 X |
| 4,778,998 | 10/1988 | Carnahan | 250/423 P |
| 4,780,284 | 10/1988 | Lovelock | 422/54 X |
| 4,804,846 | 2/1989 | Hall | 250/423 P X |
| 4,888,295 | 12/1989 | Zaromb et al. | 422/98 X |

*Primary Examiner*—Robert J. Warden
*Assistant Examiner*—Amalia Santiago
*Attorney, Agent, or Firm*—Morrison Law Firm

[57] ABSTRACT

A dual-column, dual-detector gas detector and analyzer employs both a photo-ionization detector and a flame-ionization detector. In a survey mode, samples of ambient air are driven through both detectors, and the outputs of both detectors are used to determine the presence of one or more gasses. In analysis mode, fixed-volume samples of ambient air are driven through two elution columns having different properties. The output of each elution column is fed to one of the detectors. The arrival times of gas peaks at the two detectors are employed to develop two lists of candidate gasses. The lists are cross-checked for the presence of each candidate on both lists. Candidates identified from their presence on both lists are identified. A further check attempts to identify candidates which are identifiable from their presence on one of the lists, and not on the other. Components identified in this way are added to the final list. Unidentified components are discarded, although their presence is noted and reported as unknown. Portability is retained by eliminating isothermal ovens and by reducing the quantity of hydrogen required. A simplified way of characterizing temperature corrections of elution columns is disclosed.

6 Claims, 12 Drawing Sheets

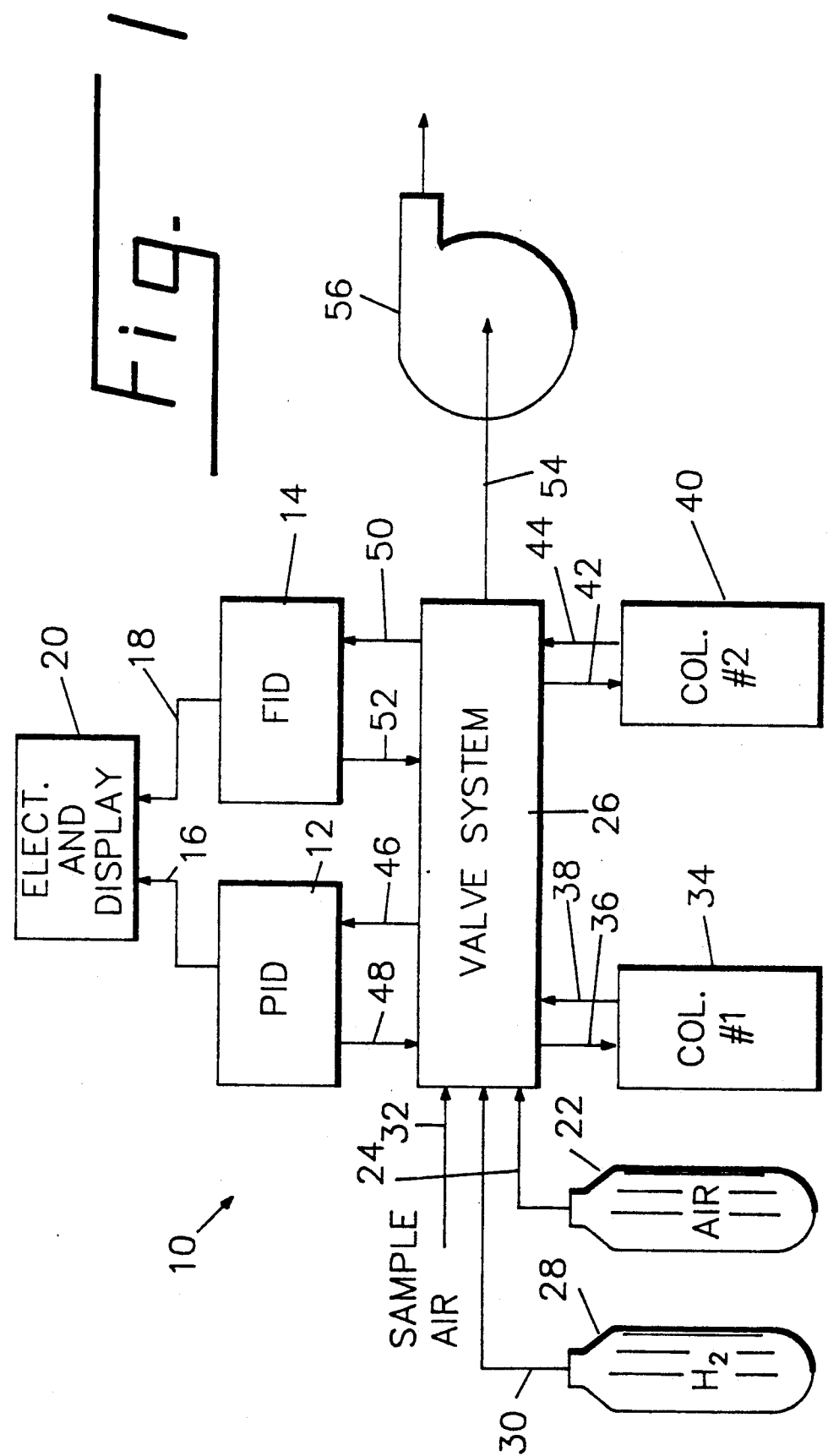

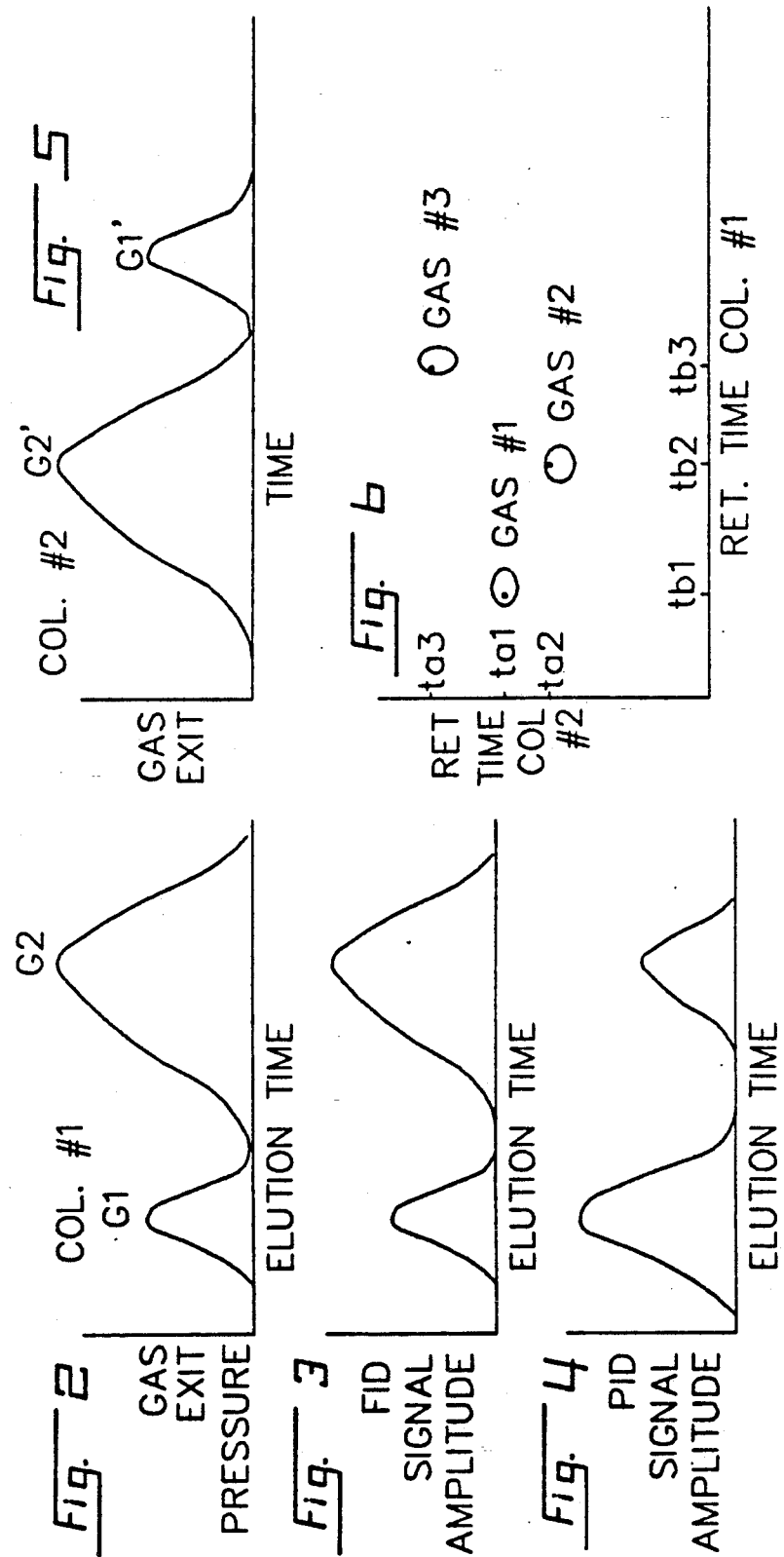

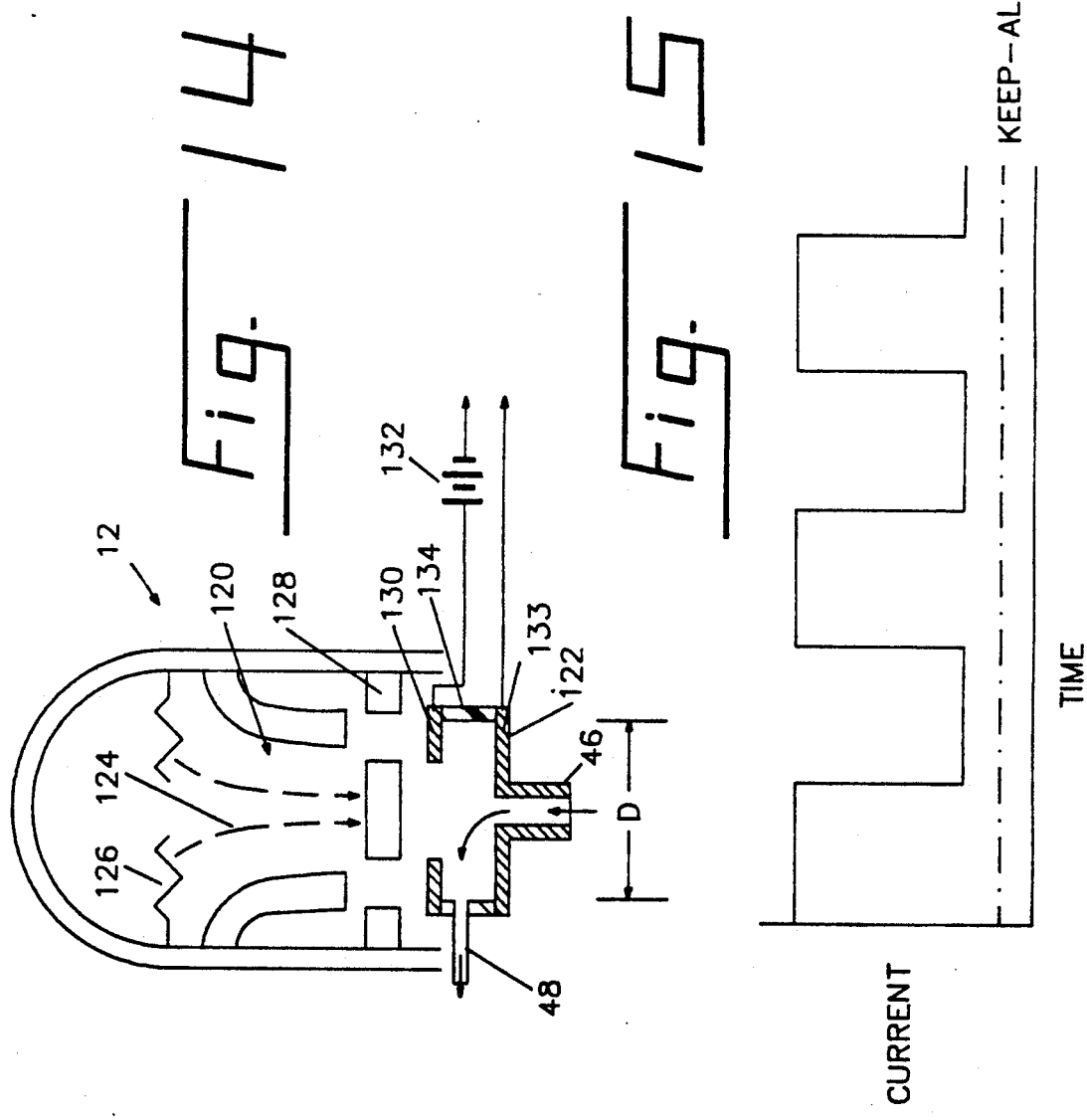

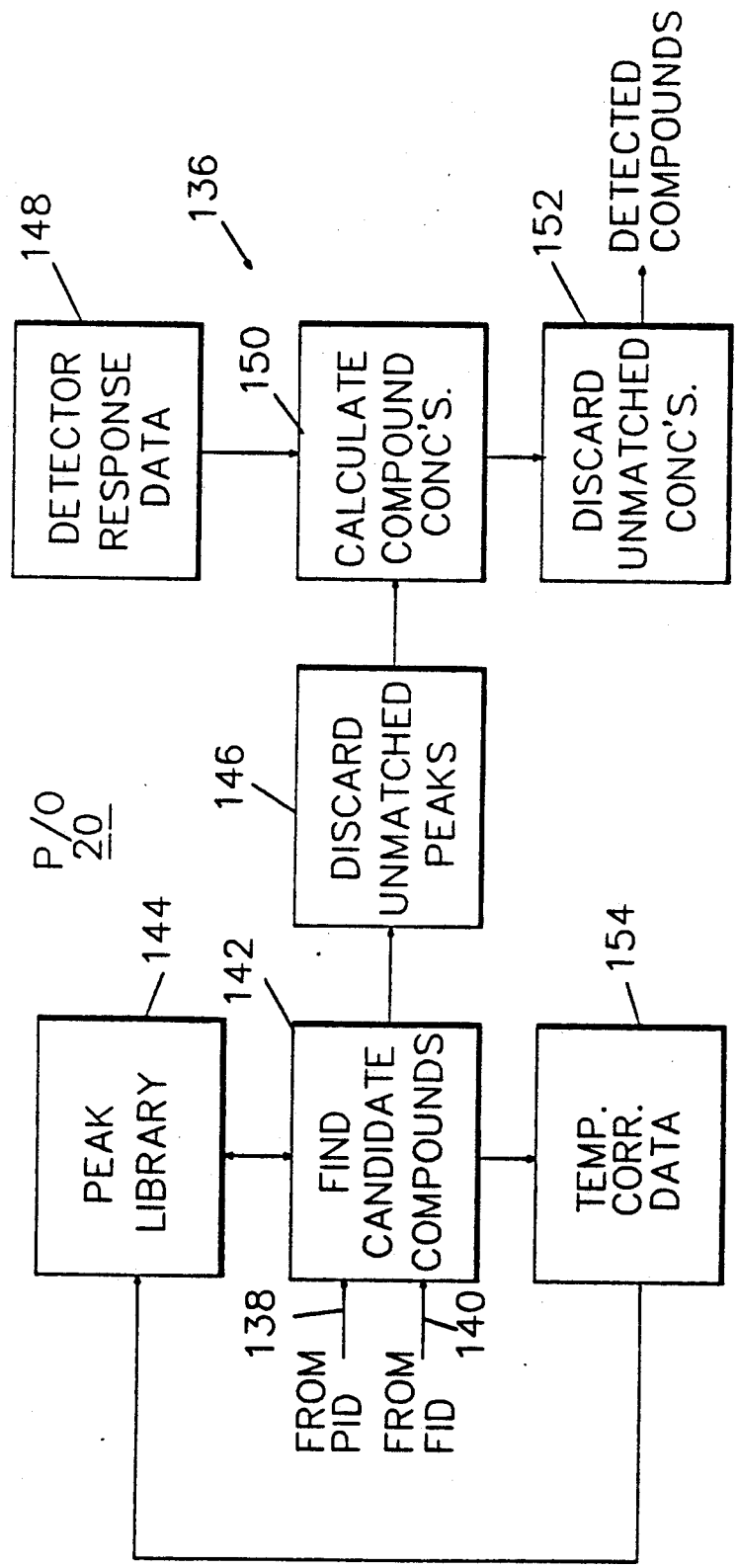

DUAL-COLUMN, DUAL-DETECTOR GAS DETECTOR AND ANALYZER

BACKGROUND OF THE INVENTION

The present invention relates to gas detectors and analyzers.

Gas detectors are employed for detecting the presence of one or more gases. In one common use, a gas detector is used to detect the presence of a gas in ambient air. One type of gas detector includes a sample chamber into which a sample of the ambient air is admitted. A source of radiant energy such as, for example, infra-red energy, is projected through the sample. A detector, responsive to the radiant energy in a spectral region which the gas is expected to absorb, receives the radiant energy after it has traversed the sample one or more times. The presence of the gas is sensed by the reduced response of the detector caused by the absorption of the radiant energy after having passed through the sample chamber.

A single gas may be identified if its absorption occurs in a spectral region not shared by absorption of other gasses in the sample. Spectral filtering reduces the spectral bandwidth of the radiant energy to that in which the single gas is expected to produce absorption. Thus, any reduction in the received signal is accepted as evidence of the existence of the gas. The magnitude of the absorption is evidence of the concentration of the gas. The presence of more than one gas having overlapping absorption spectra prevents this type of identification.

Another type of gas detector, called a photo-ionization detector, ionizes the gas using radiant energy such as, for example, ultra-violet light. A further type, called a flame-ionization detector, ionizes the gas by contacting it with a hydrogen flame. In both types of ionization detectors, the presence of the gas is detected by an increased electric current in an external circuit These detectors share the same problem of discrimination and confusion as noted in the foregoing paragraph.

One method used in the prior art for identification of gasses takes advantage of the different times required for gasses to pass through a column having an active internal surface such as, for example, an internal surface coated with a sorbant material such as a wax or polyester. A fixed volume of air suspected of containing a gas to be tested, is admitted to a long tubular column. Then, a flow of a clean gas such as, for example, clean hydrogen, is pumped at a fixed rate through the column. Different gas components are retarded by the active surface in the column so that they exit spread out in time, in a manner related to the nature of the coating and the molecular structure of the gas components. Air passes through most columns substantially without retardation. A detector sensing the output of the column produces an output signal varying over time in response to the peaks and valleys of gas components exiting the column.

A knowledge of the elution times characteristic of a coating with respect to particular gasses permits discrimination of a specific gas from among a small group of suspected gasses. Overlapping elution times of different gasses complicates the identification process. In general, the detector output signal contains insufficient information from, which the components of an unknown gas mixture can be identified.

Positive identification of gasses in an unknown mixture is possible in a laboratory environment using, for example, a mass spectrometer. Such devices are neither portable, nor useful in the field, where gas leaks must be detected and analyzed Detectors sensing the outputs of elution columns have found use in the field, but their problems of limited identification capability have not been solved. In addition, conventional analysis devices require such large supplies of compressed gas that either their portability or their operating time is limited. Finally, most gas detection and analysis devices avoid effects of ambient temperature changes by using an electric heater to maintain temperature-sensitive portions of the instrument at a constant temperature. Such an electric heater consumes quantities of electricity that are inconsistent with portable operation.

OBJECTS AND SUMMARY OF THE INVENTION

It is an object of the invention to provide a gas detection and identification apparatus which overcomes the drawbacks of the prior art.

It is a further object of the invention to increase the number of dimensions a gas-identification apparatus has available for identifying mixed, unknown, gasses.

It is a further object of the invention to provide a gas-identification apparatus employing at least first and second elution columns lined with different materials having different elution times for at least one gas component. A first gas detector senses the output of the first column. A second gas detector senses the output of the second column. The first and second gas detectors are of different types giving different responses to the same eluted gas components. The output of the first column and first detector give a first response from which a first list of candidate gasses can be assembled. The output of the second column and second detector give a second response from which a second list of candidate gasses can be assembled. Candidates on both lists form a final candidate list. The measured concentrations of the gasses in the final candidate list prunes the list to a final identification.

It is a still further object of the invention to provide a portable gas-detection and gas-identification apparatus requiring a small supply of consumables to permit extended field use in a person-carried unit.

It is a still further object or the invention to provide a flame-ionization detector requiring a smaller flow of hydrogen gas for its operation.

It is a still further object of the invention to provide a photo-ionization detector capable of utilizing a flow of hydrogen gas compatible with high-speed capillary chromatography.

It is a still further object of the invention to provide a photo-ionization detector including means for separating a wall-conduction signal from an ionization signal.

It is a still further object of the invention provide a photo-ionization detector including an arc discharge employing a pulsed current source. The pulsed current source produces varying output levels in dependence on the amount of a gas component in a detector cell. The resulting AC signal is detectable in the presence of a much larger wall-conduction signal.

Briefly stated, the present invention provides a dual-column, dual-detector gas detector and analyzer employing both a photo-ionization detector and a flame-ionization detector, In a survey mode., samples of ambient air are driven through both detectors, and the outputs of both detectors are used to determine the presence of one or more gasses In analysis mode, fixed-volume samples of ambient air are driven through two elution columns having different properties. The output of each elution column is fed to one of the detectors. The arrival times of gas peaks at the two detectors are employed to develop two lifts of candidate gasses. The lists are cross-checked for the presence of each candidate on both lists. Candidates identified from their presence on both lists are identified. A further check attempts to identify candidates which are identifiable from their presence on one of the lists and their absence from the other. Components identified in this way are added to the final list. Unidentified components are discarded, although their presence is noted and reported as unknown. Portability is retained by eliminating isothermal ovens and by reducing the quantity of hydrogen required. A simplified way of characterizing temperature corrections of elution columns is disclosed.

According to an embodiment of the invention, there is provided a gas detection system comprising: a first gas detector of a first type, the first gas detector including first means for producing a first electronic signal responsive to the presence of a gas, a second gas detector of a second type, different from the first type, the second gas detector including second means for producing a second electronic signal responsive to the presence of the gas, and means responsive to one or both of the first and second electronic signals for indicating a presence of the gas.

According to a feature of the invention, there is provided a gas analyzer comprising: a first elution column of a type effective for selectively retarding passage of at least a first gas component therethrough for a first time, a first gas detector of a first type, means for connecting gasses exiting the first elution column to an input of the first gas detector, a second elution column of a type effective for selectively retarding a passage of the at least a first gas component therethrough for a second time, the first and second times being different, a second gas detector of a second type different from the first type, means for connecting gasses exiting the second elution column to an input of the second gas detector, means for passing predetermined sample volumes of a carrier gas which may contain some of the at least a first gas component through the first and second elution columns, the first and second gas detectors having first and second amplitude responses to the at least a first gas component, and means based on the first and second times and the first and second amplitude responses for identifying the at least a first gas component.

According to a further feature of the invention, there is provided a method for detecting a gas component comprising: passing the gas through a first gas detector of a first type, producing a first electronic signal in the first gas detector in response to the presence of the gas, passing the gas through a second gas detector of a second type different from the first type, producing a second electronic signal in the second gas detector in response to the presence of a gas, and detecting the gas based on a response of one or both of the first and second electronic signals for indicating a presence of the gas.

According to a still further feature of the invention, there is provided a method for analyzing a gas comprising: passing a first predetermined sample volume of the gas through a first elution column of a type effective for selectively retarding passage of at least a first gas component therethrough for a first time, passing an output of the first elution column to a first gas detector of a first type, passing a second predetermined sample volume of the gas through a second elution column of a type effective for selectively retarding a passage of the at least a first gas component therethrough for a second time, the first and second times being different, passing an output of the second elution column through a second gas detector of a second type different from the first type, the first and second gas detectors having first and second amplitude responses to the at least a first gas component, and identifying the at least a first gas component based on the first and second times and the first and second amplitude responses.

According to a still further feature of the invention, there is provided a gas detector and analyzer comprising: a first gas detector of a first type, a second gas detector of a second type different from the first type, means for passing a flow of a sample gas through the first and second gas detectors, means in the first and second gas detectors for producing first and second electronic signals in response to at least a first gas components passing therethrough, means for indicating a presence of the at least a first gas component in response to either one or both of the electronic signals, a first elution column of a type effective for selectively retarding passage of the at least a first gas component therethrough for a first time, means for connecting gasses exiting the first elution column to an input of the first gas detector, a second elution column of a type effective for selectively retarding a passage of the at least a first gas component therethrough for a second time, the first and second times being different, means for connecting gasses exiting the second elution column to an input of the second gas detector, means for passing predetermined sample volumes of a carrier gas which may contain some of the at least a first gas component through the first and second elution columns, the first and second gas detectors having first and second amplitude responses to the at least a first gas component, and means based on the first and second times and the first and second amplitude responses for identifying the at least a first gas component.

According to a still further feature of the invention, there is provided a flame-ionization detector comprising: a burner tube, means for connecting a supply of hydrogen gas to the burner tube, a chimney surrounding the burner tube, means for passing a flow of air through the chimney sufficient to sustain combustion of the hydrogen gas from the burner tube, a discharge chamber, means for passing effluent from the chimney into the discharge chamber, means for passing a flow of purging air through the discharge chamber, the flow of purging air being sufficient to avoid a dew point in the discharge chamber, and the discharge chamber being isolated from the flow of air in the chimney to prevent interference of the purging air with the combustion.

According to yet another feature of the invention, there is provided a photo-ionization detector for detecting at least one gas component in a gas mixture comprising: a source of radiation, the radiation being of a type capable of ionizing the at least one gas component, a detector cell, means for flowing the gas mixture through the detector cell, mean for impinging the radiation on the gas mixture in the detector cell, means for permitting an electric current produced by ionization of the at least one gas component in the detector cell to flow in an external circuit, the electric current being responsive to an intensity of the radiation, means for varying the intensity between first and second predetermined limits, and the electric current being varied between first and second limits dependent on an amount of the at least one gas component, whereby an amount of ionization produced is measurable in the presence of other electric currents not responsive to the ionization.

According to a still further feature of the invention, there is provided a temperature responsive pressure regulator for controlling a pressure of a gas, comprising: a sealed chamber, a delivery chamber, a flexible diaphragm sealing an interface between the sealed chamber and the delivery chamber, a seat, a seal member sealably engageable with the seat, the seat providing communication between a pressurized source of the gas and the delivery chamber, a pressurized gas in the sealed chamber tending to urge the flexible diaphragm toward the delivery chamber, resilient means biasing the flexible diaphragm in a direction for increasing a pressure in the sealed chamber, whereby the pressurized gas acts as a gas spring in opposition to the resilient means, means for engaging the seal member with the seat in response to motion of the diaphragm, and a magnitude of the pressure in the sealed chamber and a force of the resilient means being selected to produce a change in pressure in the delivery chamber effective to maintain a mass flow rate of the gas at a substantially constant value over a temperature range.

According to a still further feature of the invention, there is provided a method for compensating for temperature variations on elution times in an elution column, comprising measuring elution times of a candidate list of at least two compounds at least two temperatures in an elution column to produce measured elution times, characterizing a nominal set of elution times for the at least two compounds on the elution column as a series of substantially straight lines formed as a natural logarithm of retention times of the at least two compounds in the elution column versus a function of temperature, the nominal set forming predicted elution times of the at least two compounds, and correcting the predicted elution times by adjusting the measured elution times along the straight line to temperature which is a function of the temperature of first and second times, wherein the first time is a time at which the compounds enter the elution column and the second time is a time at which a peak of response for a compound is attained.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1 is a schematic diagram of a gas detector and analyzer according to an embodiment of the invention.

FIG. 2 is a curve showing exit times of two gas components from one of the elution columns of the gas detector and analyzer of FIG. 1.

FIG. 3 is a curve showing a response of one detector to the gas components of FIG. 2.

FIG. 4 is a curve showing a response of a second detector to the gas components of FIG. 2.

FIG. 5 is a curve showing the exit times of the same two gas components from the other of the elution columns of the gas detector and analyzer of FIG. 1.

FIG. 6 is plot of retention times for two different elution columns for several gas components.

FIG. 14 is a schematic diagram of a photo-ionization detector of FIG. 1.

FIG. 15 is a curve showing the current applied to the photo-ionization detector of FIG. 14.

FIG. 16 is a functional block diagram of an analysis processor forming part of the electronics and display module of FIG. 1.

DETAILED DESCRIPTION OF THE PREFERRED EMBODIMENT

Figure 7:
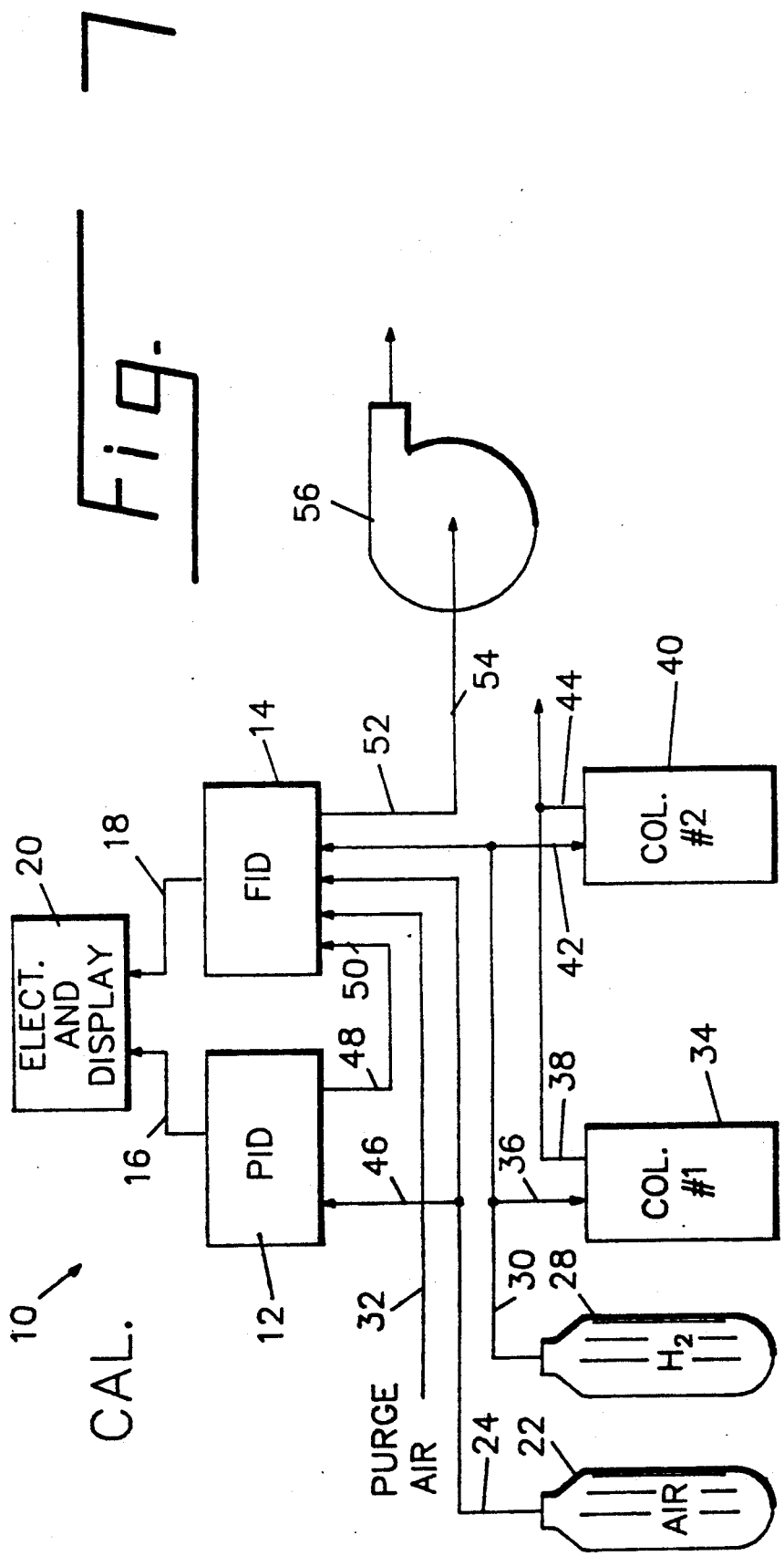
FIG. 7 is a simplified schematic diagram of the apparatus of FIG. 1 wherein the connections made by the valve system of FIG. 1 to establish a zero calibrate mode are shown.

Referring to FIG. 1, there is shown, generally at 10, a gas detector and analyzer includes a photo-ionization detector 12 and a flame-ionization detector 14 in the same instrument. Outputs of photo-ionization detector 12 and flame-ionization detector 14 are applied on lines 16 and 18, respectively to inputs of an electronics and display module 20. A pressurized air container 22 is connected by a line 24 to a valve system 26. Similarly, a pressurized hydrogen container 28 is connected by a line 30 to valve system 26. An ambient-air line 32 is connected to valve system 26 for reasons which will become evident upon further reading.

A first elution column 34 receives gas from valve system 26 on an input line 36 and returns gas to valve system 26 on a return line 38. A second elution column 40 receives gas from valve system 26 on a input line 42 and returns gas to valve system 26 on a return line 44. Valve system 26 supplies gas to photo-ionization detector 12 on a line 46 and receives gas from photo-ionization detector 12 on a line 48. Valve system 26 also supplies gas to flame-ionization detector 14 on a line 50 and receives gas from flame-ionization detector 14 on a line 52. An air exit line 54 is connected from valve system 26 to an air pump 56 for drawing air through the apparatus and discharge of air and certain by-products of the apparatus to the atmosphere.

Gas detector and analyzer 10 has three major modes of operation, namely 1) calibration, 2) survey and 3) analysis modes. Valve system 26 provides the piping changes needed for controlling the flow of the several gasses required by each mode. First elution column 34 and second elution column 40 are active only during the analysis mode. In all other modes these elements receive a purging flow of hydrogen gas from pressurized hydrogen container 28 to maintain them in a cleared condition permitting operation in analysis mode when required.

As noted in the background of the invention, analysis (identification of the constituents of an unknown gas mixture) is complicated by the possibility of confusion between the responses of a detector to the gasses. One technique for at least partly solving this problem includes passing a fixed volume of the gas mixture into an elution column and then passing a flow of a carrier gas such as, for example, hydrogen through the column. The walls of the elution column are coated with a material which selectively retards passage of different gasses through the column. Thus, the different gas components exit the elution column spread out in time in a predictable manner. The inventors have noted that some types of coatings such as, for example, a wax product sold under the trademark CAREOWAX (a trademark for polyethylene glycols and methoxypolyethylene glycols) by the Union Carbide Corporation, selectively retards polar groups of gasses, and thus increases their residence times in an elution column. Conversely, other coatings such as, for example, a methyl silicone polymer sold by the Dow Chemical Co., selectively retards non-polar gasses and increases their residence time in the elution column. Thus, the exit time of the peak concentration of a gas component is related to the nature of the gas component and to the type of coating on the elution column. As also noted in the background of the invention, a single detector type, sensing the gas components exiting either type of elution column, although capable of a limited amount of discrimination of multiple gasses, is still severely limited in its ability to discriminate a large number of unknown gasses.

The inventors have recognized that additional dimensions in an identification technique is available through the use of two different types of elution columns. That is, first elution column 34 may employ, for example, a coating effective for selectively retarding non-polar gasses and second elution column employs a coating effectively for selectively retarding polar gasses, or vice versa. Comparing the times at which the peaks of gas components exit first elution column 34 and second elution column 40 permits additional discrimination. Applying a priori knowledge of the amount by which each gas component may be retarded by the two different types of coatings adds substantially to the information gained from detecting the gas components exiting first elution column 34 and second elution column 40.

The inventors have further recognized that different types of detectors respond differently to different gas components. That is, a particular gas component may produce a strong response in photo-ionization detector 12 and may produce a weaker response (or no response at all) in flame-ionization detector 14 and vice versa. Thus, if photo-ionization detector 12 is connected to measure gas components exiting first elution column 34, and flame-ionization detector 14 is connected to measure gas components exiting second elution column 40, the different responses of photo-ionization detector 12 and flame-ionization detector 14 to identical gas components adds a still further dimension to the information available for analysis of an unknown mixture.

Referring to FIGS. 2 a curve illustrates the partial pressures of two gasses G1 and G2 exiting first elution column 34. It will be noted that, although both gas components entered first elution column 34 at the same time, the elution of gasses G1 and G2 are separated in time by the coating in first elution column 34. FIGS. 3 and 4 illustrate the detection signals that flame-ionization detector 14 and photo-ionization detector 12, respectively, would produce if the exiting gasses in FIG. 2 were fed to these elements. It will be noted that the peaks of these detection signals occur at times coinciding with the peaks of their gas concentrations but the peaks are markedly different in amplitude.

Referring now to FIG. 5, the times which gas components G1 and G2 exit second elution column 40 are illustrated. It is assumed that the coating in second elution column 40 is of a type which retards gas G1 more than it does gas G1. As a result, the times of the peaks of gasses G1 and G2 are reversed from those exiting first elution column 34 (FIG. 2). It will be noted that the areas of the exiting gas concentrations are substantially the same in FIGS. 2 and 5 provided that equal sample volumes have been injected into each column, and thus equal volumes must exit.

The differences in times and amplitudes of the signals detected from gasses exiting the two elution columns permit inferences to be made regarding the identities of the gasses producing the signals.

Referring now to FIG. 6, in response to a plurality of unknown gasses, the apparatus may give the results shown. Prior knowledge of the amount by which the coatings in first and second elution columns 34 and 40 retard the gas components permits estimates to be made of the probable exit times of peak concentrations of a number of gasses. These estimates are represented by ellipses. That is, each closed ellipse represents the expected range of retention times for first and second elution columns 34 and 40 for one gas component having traversed the paths discussed above. If a peak from one elution column falls within an ellipse, then it is a candidate, if it falls outside, then it is retained for possible single-peak identification. As the next step in the screening, if a peak exiting first elution column 34 falls within an ellipse, then a peak for the same gas component exiting second elution column 40 must also be found to fall within an ellipse, and vice versa. If a gas component is of a type to which one of the detectors is insensitive, then the existence of a peak in the non-sensitive detector is not required, and its presence in one detector and its absence from the other may be used as the identification criterion. If neither identification technique is capable of attaining an identification, then the existence of the peak is noted and reported, but the peak is considered discarded as unidentifiable.

Once the candidates are determined, false positives are reduced by comparing the amplitudes of the detected signals in the two different detector types. The relative amplitudes of the signals produced by a given gas component are known. Signals assumed to be produced by a candidate gas that cannot be confirmed by relative signal amplitudes, may have been produced by a coincidental presence of one or more unknown gasses to which the apparatus is sensitive. The term unknown is intended to mean gasses for which relative retention times and relative amplitudes have not been entered into the system. It is contemplated that different libraries of retention times and amplitude relationships may be employed for different purposes. Thus, a gas may be in one library and not in another. A gas appearing only in the second library is not identified when the first library is in use.

It would be clear to one skilled in the art that the additional sorting of candidates resulting from comparing signal amplitudes from the two detectors may be dispensed with in some circumstances. In this case, relative retention times alone are relied on for identification. This may be acceptable when the presence of only a few well-known candidates are expected.

Referring now to FIG. 7, gas detector and analyzer 10 is shown in the zero calibrate mode, wherein the connections made through valve system 26 are indicated. During zero calibrate mode, first and second elution columns 34 and 40 both receive a flushing flow of hydrogen gas from line 30. The hydrogen gas is discharged through return lines 38 and 44. Clean air from pressurized air container 22 passes along line 24 and enters photo-ionization detector 12 through line 46. Line 48 connects the air exiting photo-ionization detector 12 to line 50 for admission to flame-ionization detector 14. A supply of ambient purge air is connected on ambient-air line 32 to flame-ionization detector 14. Also, a small flow of pure air from pressurized air container 22, as well as a flow of hydrogen from pressurized hydrogen container 28 are applied to flame-ionization detector 14. The signals generated in photo-ionization detector 12 and flame-ionization detector 14 are applied on lines 16 and 18 to electronics and display module 20, wherein they are used for calibration based on measurements taken from the sample of clean air flowing through both of these devices.

As will be developed in later paragraphs, flame-ionization detector 14 burns hydrogen gas in the presence of the gas to be tested. The burning hydrogen gas ionizes gas components in the mixture. A current is measured as a result of the ionized components. This current is the basis of the measurement. The purge air is a relatively large flow of ambient air employed to carry off the water vapor produced by burning hydrogen in air, plus gasses in the mixture whereby the dew point in flame-ionization detector 14 remains below the temperature maintained therein. Since the materials exiting air exit line 54 contain the purge air and the products of combustion of the flame, it is important that, when photo-ionization detector 12 and flame-ionization detector 14 are connected in series, photo-ionization detector 12 be connected in the upstream position shown. Otherwise, consumption of the gasses in the sample and pollution from flame-ionization detector 14 would corrupt measurement in photo-ionization detector 12.

The serial connection shown in use during analysis mode may be replaced with a parallel connection of gas samples exiting first and second elution columns 34 and 40 to photo-ionization detector 12 and flame-ionization detector 14, respectively. Such a parallel connection is the preferred embodiment during analysis mode.

Figure 8:
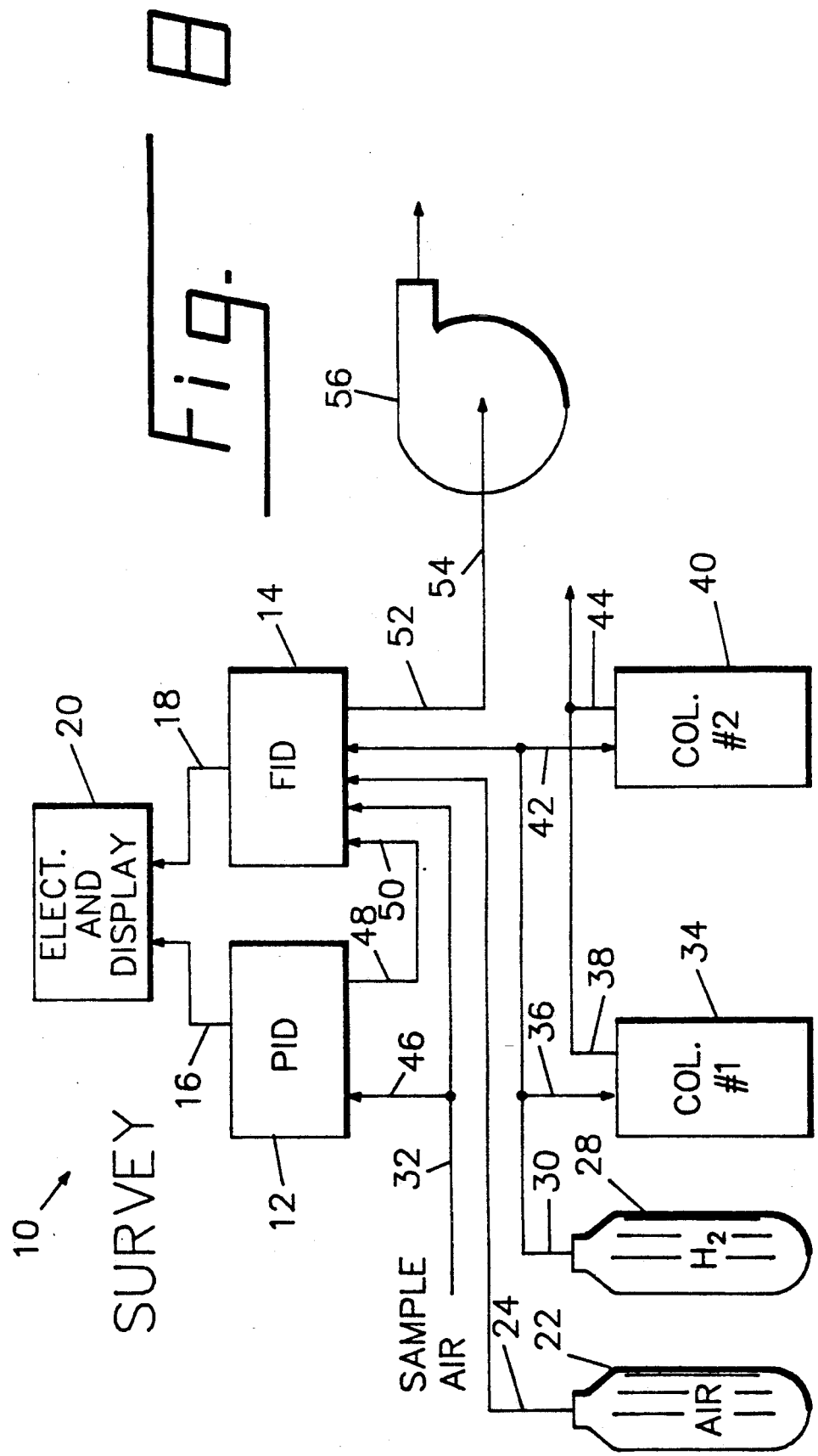
FIG. 8 is a simplified schematic diagram of the apparatus of FIG. 1 wherein the connections made by the valve system of FIG. 1 to establish a survey mode are shown.

Referring now to FIG. 8, gas detector and analyzer 10 is shown with the connections made for the survey mode. Sample air to be tested is admitted from ambient-air line 32 and line 46 to photo-ionization detector 12. After exiting photo-ionization detector 12 the sample air is connected through line 48 and line 50 for input to flame-ionization detector 14. As previously noted, purge air and hydrogen are required for operation of flame-ionization detector 14. These are supplied on ambient-air line 32 and line 30, respectively. A small flow of clean air from pressurized air container 22 may be connected on line 30 to flame-ionization detector 14. The effluent from flame-ionization detector 14 is drawn through line 52 and air exit line 54 by air pump 56 for discharge to the atmosphere. Signals from photo-ionization detector 12 and flame-ionization detector 14 are connected on lines 16 and 18 to electronics and display module 20.

As noted in the description of the background of the invention, photo-ionization detector 12 and flame-ionization detector 14 respond differently to different gas components. One may be completely insensitive to a gas component which the other is capable of detecting without difficulty. Operating both detectors in parallel in the manner shown permits detection of any gas component detectable by either or both of photo-ionization detector 12 and flame-ionization detector 14. In most cases, when one or more gas components are detected in the survey mode, only an indication of gas presence, as well as an indication of gas concentration, are produced. Identification is seldom possible in this mode.

During survey mode, first and second elution columns 34 and 40 are kept flushed by a reverse flow of hydrogen from pressurized hydrogen container 28.

Analysis mode can be thought of as occurring in two steps. First, in a charging step, two sample volumes are filled with the gas mixture to be analyzed. Then, in an analyze step, the gas mixtures in the two sample volumes are driven through respective elution columns en route to their respective detectors.

Figure 9:
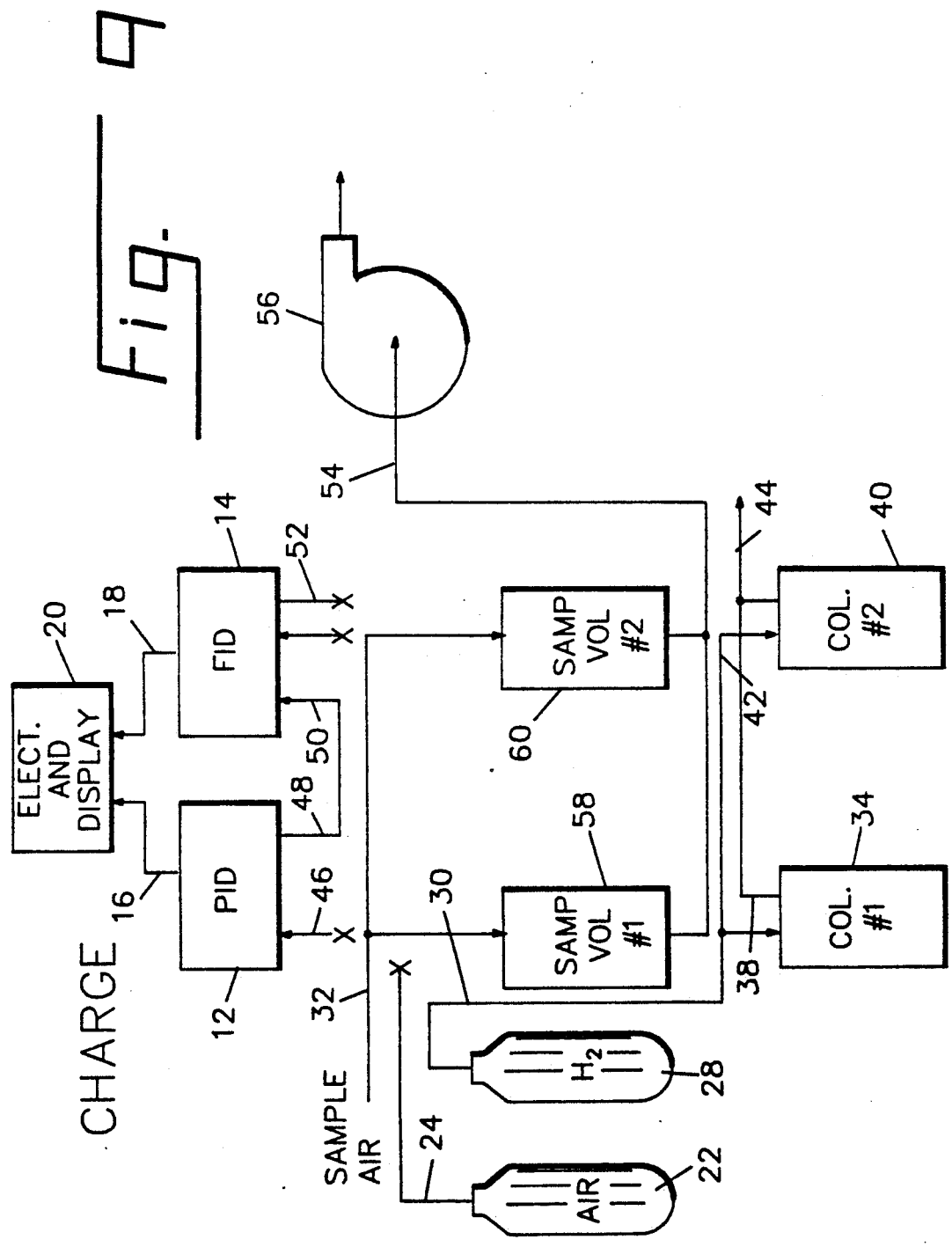
FIG. 9 is a simplified schematic diagram of the apparatus of FIG. 1 wherein the connections made by the valve system of FIG. 1 to establish the charge step of the analysis mode are shown.

Referring to FIG. 9, gas detector and analyzer 10 is shown as connected for the charging step. First and second elution columns 34 and 40 continue to receive a purging flow of hydrogen from pressurized hydrogen container 28. A first sample volume 58 and a second sample volume 60 are connected between ambient-air line 32 and air exit line 54. Operation of air pump 56 draws the gas mixture to be analyzed through first and second sample volumes 58 and 60, thereby filling them with the gas mixture to be analyzed.

Figure 10:
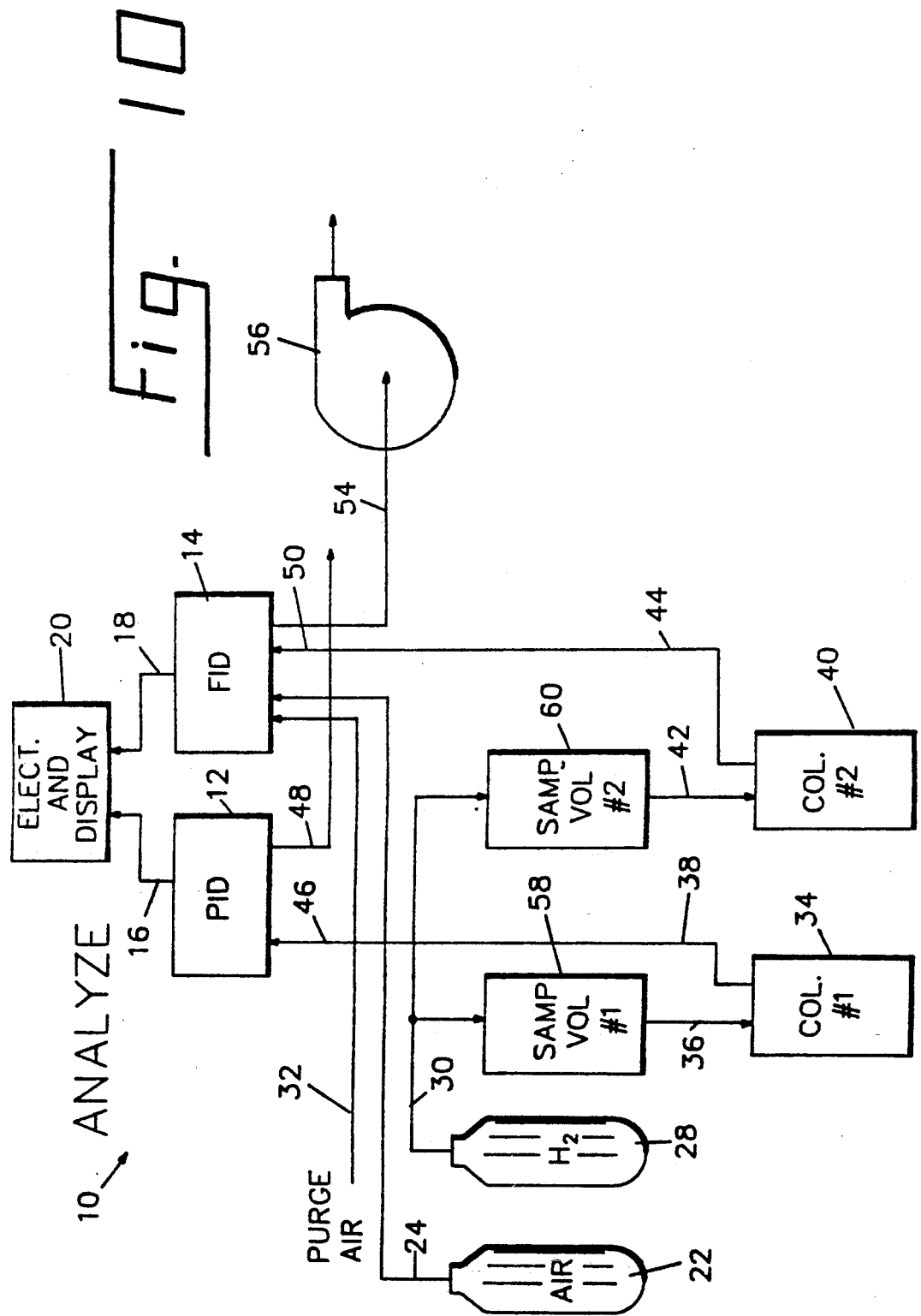
FIG. 10 is a simplified schematic diagram of the apparatus of FIG. 1 wherein the connections made by the valve system of FIG. 1 to establish the analyze step of the analysis mode are shown.

Referring now to FIG. 10, at the end of the charging step of FIG. 9, fixed predetermined volumes of sample gas are contained in first and second sample volumes 58 and 60. At the beginning of the analyze step shown, the connections shown are set up. The output of first sample volume 58 is connected through input line 36 to the input of first elution column 34. The output of first elution column 34 is connected on return line 38 and line 46 to the input of photo-ionization detector 12. The output of photo-ionization detector 12 is vented on line 48. Similarly, the output of second sample volume 60 is connected through input line 42 to the input of second elution column 40. The output of second elution column 40 is connected on return line 44 and line 50 to the input of flame-ionization detector 14. The output of flame-ionization detector 14 is connected through air exit line 54 to air pump 56. A controlled flow of hydrogen gas from pressurized hydrogen container 28 is connected to the input of first and second sample volumes 58 and 60.

In operation, as the hydrogen gas flows through first and second sample volumes 58 and 60, it drives the gas samples before it into, and through, first and second elution columns 34 and 40 respectively. As explained above, each gas component interacts differently with the coatings on the surfaces of first and second elution columns 34 and 40, thereby selectively retarding the gas components so that they emerge from their respective columns and into their respective detectors separated in time. The detectors then respond to the individual gas components.

Although the preceding description encourages thinking about the analysis mode as occurring in two discrete steps, this is not necessarily the case. In a commercial instrument, first and second sample volumes 58 and 60 may be maintained in series with air pump 56 at all times during the survey mode shown in FIG. 8. When the survey mode results in the detection of a gas whose identification is desired, first and second sample volumes 58 and 60 are already filled with gas samples to be analyzed. Then, the connections can be changed directly from those of the survey mode to those of the analyze step of FIG. 10.

Figure 11:
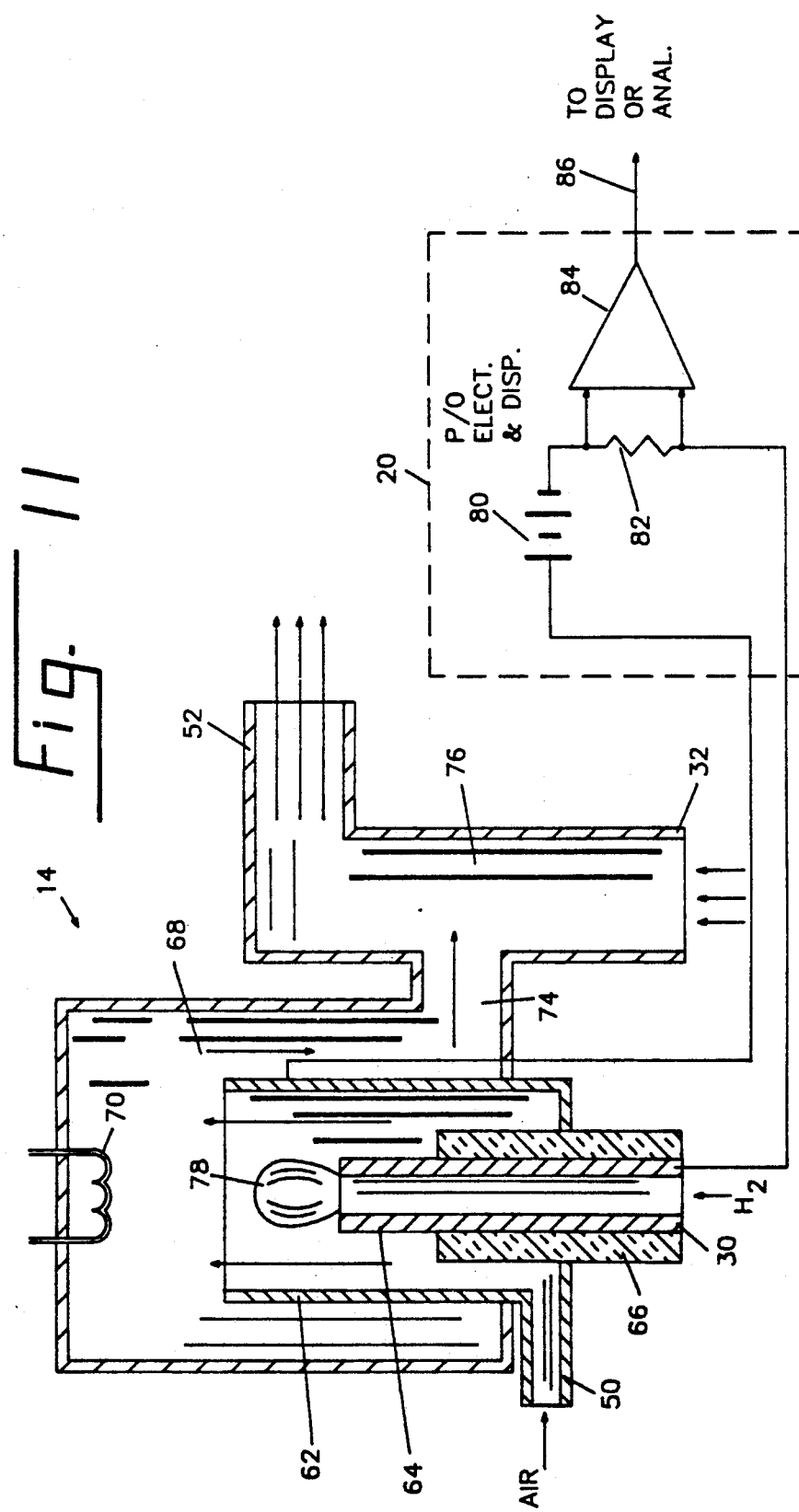
FIG. 11 is a simplified schematic diagram of the flame ionization detector of FIG. 1, showing some parts in cross section and other parts in block and schematic form.

Referring now to FIG. 11, flame-ionization detector 14 includes a chimney 62 having a burner tube 64 generally centered therein. An insulating sleeve 66 provides electrical insulation between chimney 62 and burner tube 64. An outer end of burner tube 64 is connected to line 30 to receive a controlled supply of hydrogen gas. Air is connected on line 50 to the interior of chimney 62, whereby the air flows about the perimeter of burner tube 64 before exiting through the top of chimney 62 into a discharge chamber 68. An igniter 70 is aligned with an axis of burner tube 64 in discharge chamber 68. A baffle (not shown) optionally may be employed between burner tube 64 and igniter 70 to reduce cooling of igniter 70 by air flowing therepast. The preferred embodiment of the invention dispenses with the baffle. A cross tube 74 is connected between discharge chamber 68 and a purge chamber 76. Purge chamber 76 receives a vigorous flow of purging air from ambient-air line 32 for discharge through line 52.

Igniter 70 preferably contains a material capable of exothermal catalytic action in the presence of hydrogen and oxygen. One suitable material is, for example, platinum. When oxygen (pure or in air) and hydrogen are fed into burner tube 64, a catalytic reaction of oxygen and hydrogen at the surface of the igniter 70 raises the temperature of igniter 70 toward the ignition temperature of hydrogen gas. In practice, the catalytic reaction may be insufficient, by itself, to raise the temperature of igniter 70 all the way to the ignition point of hydrogen gas.

The electrical resistance of igniter 70 varies with its temperature. Thus, an external electronic circuit (not shown), by measuring the resistance of igniter 70, can determine whether its temperature is high enough to ignite the hydrogen gas from burner tube 64, in the presence of the air from line 50. In the event that a temperature below the hydrogen ignition point is detected, an electrical pulse is applied to igniter 70 to raise its temperature sufficiently to attain ignition, whereby a flame 78 is initiated. Successful ignition is detected by the higher temperature produced by flame 78. The temperature of igniter 70 continues to be monitored to detect a loss of flame 78. If flame 78 is lost, the ignition procedure is repeated.

A DC voltage source 80 has one of its terminals connected to chimney 62 and the other of its terminals connected through a resistor 82 to burner tube 64. The terminals of resistor 82 are connected to the inputs of an amplifier 84.

During zero calibrate mode, pure hydrogen is fed to burner tube 64 and pure air is fed to chimney 62. The pure hydrogen burns in the presence of pure air to produce water vapor. Ambient air is fed to purge chamber 76 in all modes.

During survey mode, pure hydrogen is fed to burner tube 64 and a flow of ambient air is fed to chimney 62. The pure hydrogen in burner tube 64 burns in the presence of ambient air in chimney 62 to produce flame 78. If the ambient air contains contaminants capable of being ionized by flame 78, their ionization permits a current to flow between chimney 62 and 64 and in the external circuit through DC voltage source 80 and resistor 82. Current through resistor 82 produces a voltage across resistor 82 which is amplified by amplifier 84 for connection on an output line 86 to display and/or analysis portions of electronics and display module 20 (not shown).

In analysis mode, the output of second elution column 40 is fed to burner tube 64 and clean air is fed to chimney 62. It will be recalled that second elution column 40 is initially filled with purging hydrogen gas and then receives a fixed-volume sample of ambient air driven through it by hydrogen gas. The air passes through second elution column 40 undelayed except for its time of transit. Gas components, however, are selectively delayed according to the types of gasses and the type of coating in second elution column 40. Thus, the air emerges first from second elution column 40 and is fed to burner tube 64, preceded and followed by hydrogen gas bearing the eluting gas components emerging at their respective times. When the peak concentration of air reaches the flame 78, flame 78 is extinguished for a brief time. The delay time of the gas components in second elution column 40 is sufficient to permit re-ignition of flame 78 before they arrive. The hydrogen, containing the gas components at their respective times, burns with the clean air in burner tube 64. Gas components in the hydrogen capable of being ionized by flame 78 permit an ionic current to flow between burner tube 64 and chimney 62 to serve as the basis for detection of the gas component in the manner described above.

It is important to reduce the consumption of electricity and gasses to reduce the weight and extend the operating time of a person-portable device. Catalytic heating of igniter 70 by hydrogen is one way to reduce consumption of electricity. Only the amount of electricity required to raise the temperature of igniter 70 from its catalytically heated temperature to an ignition temperature is required. Once ignition is attained, a stable flame 78 is usually achieved and no further electricity should be needed for ignition.

One technique for reducing the consumption of hydrogen requires that the size of flame 78 remain as small as possible. Purge air in relatively large quantity is required to keep the exhaust products, principally water and by-products of the sample air, above the dew point and to carry them off. In the prior art, sample air flows past a flame 78 in great enough volume to serve both as sample and purge air. A relatively large flame 78 is required to maintain combustion in such a large flow of air. Prior art devices are capable of reducing hydrogen flow only to about 50 milliliters per minute. At lower hydrogen flow rates, it is difficult or impossible to maintain a stable flame. In addition, such high flow rates of air past the flame permit incomplete reaction between sample and flame, and thereby permit measurement errors to arise. An alternative way to reduce the air flow required to avoid condensation in a flame-ionization detector includes placing the apparatus in an electrically heated oven. The oven keeps the entire apparatus at a temperature above the dew point. Such a technique is clearly counterproductive from the standpoint of reducing the consumption of electricity.

In order to reduce the use of hydrogen below values permitted by the prior art, we have separated the functions of providing sample air to flame 78 and providing purge air for purging products of the process. Only the amount of sample air required for sensing is admitted to chimney 62 through line 50. This permits us to reduce the hydrogen flow to burner tube 64 to as little as about 7 milliliters per minute. The flow of sample air admitted to chimney 62 can be limited to about 30 milliliters per minute for the very small flame 78 produced. The flow of purge air through purge chamber 76 is on the order of several hundred cubic centimeters per minute. Since such purge air is kept separated from flame 78, its large flow volume has no effect on flame 78, while it remains effective to carry off the water vapor and other products. Also, during operating modes where pure air is used in the vicinity of flame, the separation of combustion and purge air permits us to use pure air only for the combustion function and to supply the relatively large purge air flow from the environment.

In some cases, it is advantageous to mix a proportion of air with the hydrogen gas before admitting it to line 30. With pure hydrogen exiting burner tube 64, only the surface of flame 78 is available for mixing combustion air with the hydrogen to attain combustion. In a very tiny flame, the surface of flame 78 may be too small to permit enough air to mix with the hydrogen gas to provide a stable flame. This may be overcome by mixing a proportion of air with the hydrogen before admitting the mixture to burner tube 64. Thus, only an additional amount of air beyond that mixed with the hydrogen, is needed for combustion. In the preferred embodiment, the amount of air mixed with the hydrogen is less than required to provide a stoichiometric mixture. Up to about 3 milliliters of air per minute is a suitable quantity to add to the flow of hydrogen to improve flame stability.

It is a problem to supply a constant mass flow rate of hydrogen over a wide range of temperatures. The viscosity of hydrogen increases and its density decreases with temperature. These effects both act in the same direction to reduce the mass flow rate of hydrogen from a conventional regulator as the temperature increases. Such a reduction may be as much as 25 percent over the normal ambient temperature variations. In zero calibrate and survey modes, hydrogen gas is supplied to flame-ionization detector 14 to ionize gas components in the sample air. In analysis mode (FIG. 10), both photoionization detector 12 and flame-ionization detector 14 receive gas components driven through their respective first and second elution columns 34 and 40 by a flow of hydrogen gas. A constant mass flow rate of hydrogen is required in all modes to attain reliable detection sensitivity and also to maintain a stable flame in flame-ionization detector 14. A variation of 25 percent in hydrogen mass flow rate is unacceptable.

In the prior art, constant hydrogen mass flow rates may be attained by keeping the instrument heated to a constant temperature in an electric oven. This is not an ideal solution in a system wherein it is desired to reduce electric power consumption.

Figure 12:
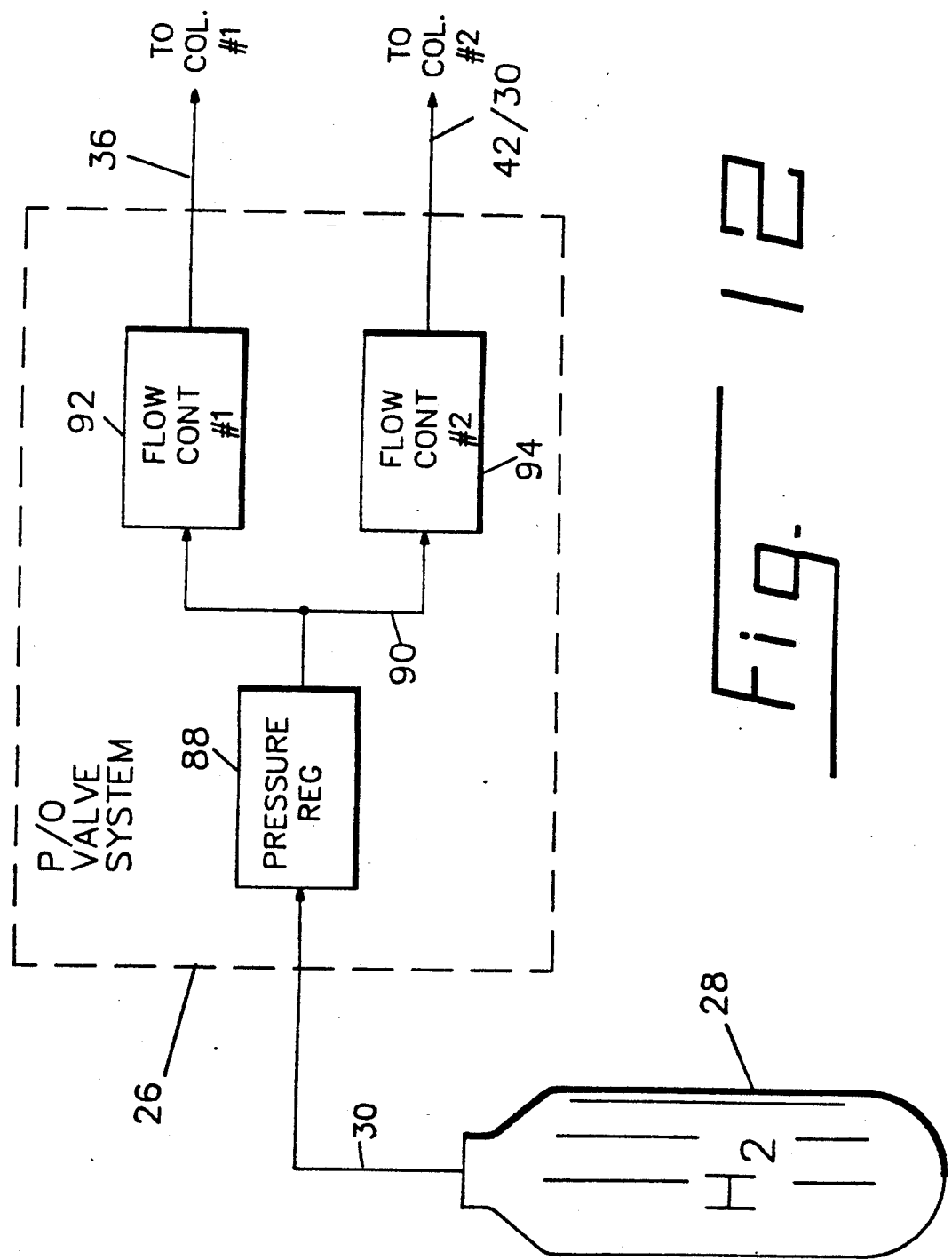
FIG. 12 is a block diagram of the hydrogen flow control portion of the valve system of FIG. 1.

Referring now to FIG. 12, a portion of valve system 26 includes a hydrogen temperature responsive pressure regulator 88 receiving hydrogen from pressurized hydrogen container 28 at an elevated pressure, and reducing the pressure to a value that varies with the ambient temperature for application on a line 90 to first and second flow controllers 92 and 94. During analysis, the outputs of first and second flow controllers 92 and 94 are applied on input lines 36 and 42 to first and second elution columns 34 and 40, respectively. During zero calibrate and survey modes, the output of second flow controller 94 is applied directly to flame-ionization detector 14. A purging flow of hydrogen gas is applied to first and second elution columns 34 and 40 during zero calibrate and survey modes.

Flow controllers 92 and 94 are assumed to be conventional and thus further description thereof is not required. Such conventional flow controllers, when fed a constant-pressure gas at varying temperature, tend to pass changing mass flow rates as the density and viscosity of the gas change with temperature. Both changes are in a sense tending to reduce the mass flow rate of gas at higher temperatures.

Figure 13:
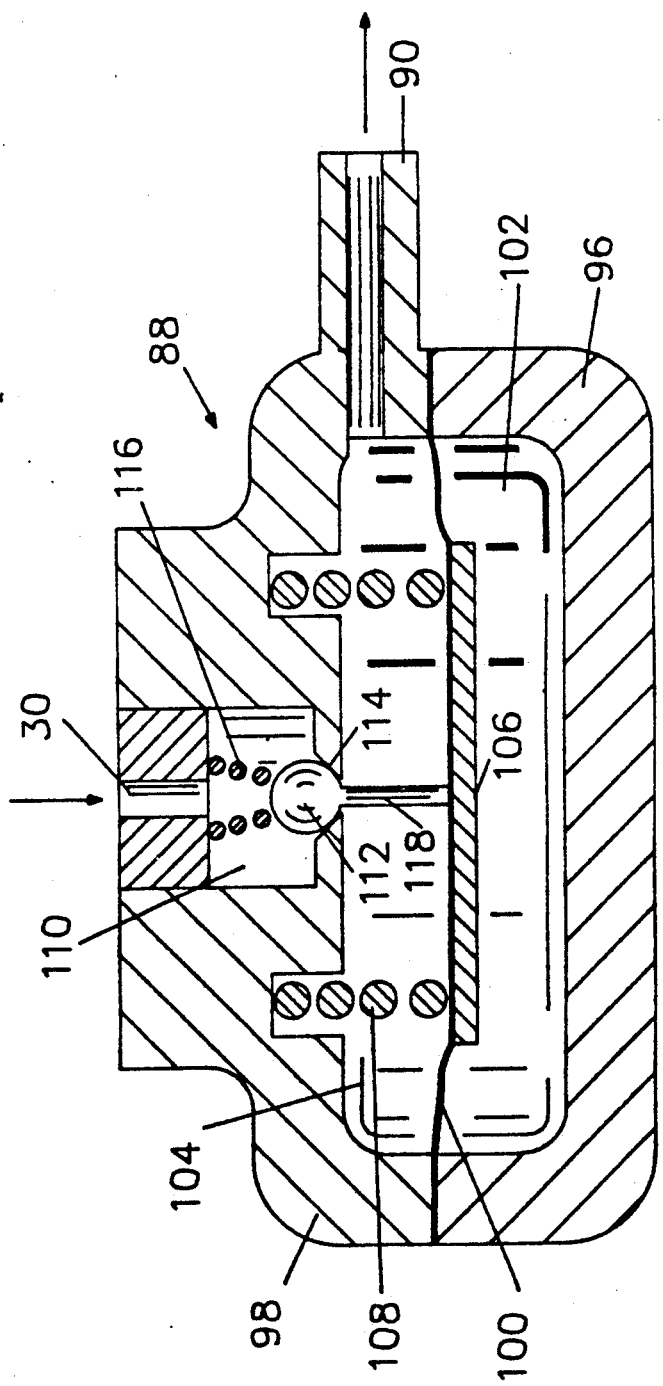
FIG. 13 is a cross section of a temperature-responsive pressure regulator of FIG. 12.

Referring now to FIG. 13, temperature responsive pressure regulator 88 includes a lower member 96 and an upper member 98 sealed gas-tight at their abutting perimeters. A flexible diaphragm 100 seals a pressurized chamber 102 below flexible diaphragm 100 from a delivery chamber 104 above it. Delivery chamber 104 is connected to line 90. A rigid plate 106 occupies a center of flexible diaphragm 100. A helical spring 108 bears downward on flexible diaphragm 100 near a perimeter of rigid plate 106. An intermediate chamber 110 receives pressure-regulated hydrogen gas from line 30. A ball seal 112 in intermediate chamber 110 is urged toward a seat 114 by a helical spring 116. A stem 118 extends downward from ball seal 112, past seat 114 toward flexible diaphragm 100.

As the pressure in delivery chamber 104 decreases, the pressurized gas in pressurized chamber 102, urges flexible diaphragm 100 upward against the combined resistance of helical spring 108 and the gas pressure in delivery chamber 104. Flexible diaphragm 100 contacts stem 118, thereby urging ball seal 112 out of contact with seat 114. This permits a flow of hydrogen past seat 114 until delivery chamber 104 contains a pressure sufficient to balance forces on flexible diaphragm 100, whereby output pressure in delivery chamber 104 is regulated.

The mass flow rate of hydrogen through conventional flow controllers 92 and 94 varies from one temperature to another as the ratio of absolute temperatures to a power of $-1.695$. A counter correction is required, varying as the ratio of absolute temperatures to a power of $+1.695$ to compensate for the reduction in mass flow rate which would otherwise take place. This counter correction is achieved by causing hydrogen pressure regulator 88 to increase its output pressure in response to increasing temperature, in an amount that causes flow controllers 92 and 94 to produce substantially constant mass flow.

A gas spring formed by a pressurized gas in pressurized chamber 102 provides the counter correction. As temperature increases, the gas pressure maintained in pressurized chamber 102 increases by about the first power of absolute temperature. This causes the pressure in delivery chamber 104 to increase by the same amount in order to maintain the balance of forces on flexible diaphragm 100. For the pressure in delivery chamber 104 to increase by the 1.695 power of absolute temperature, the absolute pressure in pressurized chamber 102 initially must be charged with about 1.695 times the absolute pressure in delivery chamber 104. The resulting unbalanced pressure forces acting on flexible diaphragm 100 are rebalanced with the aid of helical spring 108. The balancing force is just sufficient to compensate for the increased viscosity and reduced density of the gas, and thereby to maintain a constant mass flow rate in the presence of changing temperature.

Although other parameters may be chosen for other applications and nominal values, in one embodiment with an effective diameter of flexible diaphragm 100 equal to about 1.0 inch, and a desired nominal output pressure of about 70 PSIG, a pressure of about 133 PSIG is required in pressurized chamber 102 and a spring force of about 16 pounds is required from helical spring 108. This combination has been found to compensate for temperature variations over an ambient range of from about 32 to about 120 degrees F by increasing the pressure in delivery chamber 104 as a function of temperature.

Referring now to FIG. 14, photo-ionization detector 12 includes an ultra-violet source 120 and a detector cell 122. As is conventional, an arc discharge 124 is set up in a gas in ultra-violet source 120 between a cathode 126 and an anode 128. Ultra-violet light produced by arc discharge 124 impinges on the interior of detector cell 122. A top metallic plate 130 of detector cell 122 is connected to one terminal of a DC source 132. A bottom metallic plate 133 of detector cell 122 is connected through an external circuit (not shown) to the other terminal of DC source 132. An insulating wall 134 encloses detector cell 122 between top metallic plate 130 and bottom metallic plate 133. A sample gas enters detector cell 122 through line 46 and exits through line 48. Components in the sample gas in detector cell 122 are ionized by the ultra-violet light impinging thereon. The gas ions permit a current to flow between top metallic plate 130 and DC source 132 which is detected in the external circuit.

We have observed that wall conduction along insulating wall 134 between top metallic plate 130 and bottom metallic plate 133 can be several orders of magnitude greater than the ionic current produced by ionized sample gasses. Thus, a very small signal must be detected in the presence of a large noise.

The problem of wall conduction is exaggerated by the desire to use photo-ionization detector 12 in both survey and analysis modes. In survey mode, the sample gas is ambient air containing gasses to be detected. In analysis mode, the sample gas is initially air, followed by, principally, the hydrogen gas employed to drive the gas components through first elution column 34, including eluting gas components at their respective times. Ambient air is dirty, and contains water vapor as well as other contaminants. Particulate contaminants may be filtered from the air, but the water vapor enters detector cell 122 and is sorbed in insulating wall 134. This produces a large increase in wall conduction. When the sample gas changes to hydrogen, wall conduction changes as the water becomes desorbed from insulating wall 134. Without some technique for separating the contributions of wall conduction and ionic conduction from the signal applied to the external detection device, photo-ionization detector 12 would not be usable in survey mode.

We have observed that wall conduction is principally a function of the DC voltage applied between top metallic plate 130 and bottom metallic plate 133, and the contamination of insulating wall 134. However, ionic conduction in detector cell 122 is principally a function of the DC voltage and the magnitude of the incoming ultra-violet radiation. The magnitude of the ultra-violet radiation, in turn, is a function of the current between cathode 126 and anode 128.

Referring now also to FIG. 15, a curve shows that the current between cathode 126 and anode 128 is varied as a function of time between predetermined upper and lower limits. The upper limit is set to obtain maximum ionization in detector cell 122. The lower limit remains above a keep-alive current, whereby arc discharge 124 is not extinguished at any time during normal operation. The magnitude of ultra-violet radiation generated in ultra-violet source 120 generally follows the applied currents. Thus, ionic conduction in detector cell 122 also generally follows the current applied between cathode 126 and 128, while wall conduction remains unaffected by this current. The magnitude of ionic conduction is thus detectable in external detection circuits by sensing the AC component in the total signal from detector cell 122.

Although the above technique is understood to be an innovative approach to overcoming the effects of wall conduction, other techniques may be employed without departing from the spirit and scope of the invention. For example, instead of pulsing the current between two levels, both above the keep-alive level, the current may be simply pulsed on and off. One disadvantage of this is the extinction of arc discharge 124 between pulses. Since striking arc discharge 124 usually takes a short, variable time, and since arc discharge 124 is usually unstable for a short time after striking, this is not a desired alternative. Mechanical, optical, electro-optical, radio or other types of chopping of the exciting radiant energy impinging on the contents of detector cell 122 may also be considered part of the present invention.

Returning to FIG. 14, the problem of reducing the consumption of hydrogen gas is also addressed in photo-ionization detector 12. It is desired to reduce the flow of hydrogen gas during analysis mode to a rate equal to that in flame-ionization detector 14 (about 7 milliliters per minute). The same flow of sample air is used during survey mode. Such a small flow implies that only very small quantities of gas components are available within detector cell 122. Although reducing the diameter D of detector cell 122 could compensate for the reduced gas flow, it is common knowledge that this would also reduce the ionic signal, since the volume of gas available for ionization varies with the volume of detector cell 122. We nevertheless reduced diameter D from about one-eighth inch to about one-sixteenth inch. As expected, the ionic conduction signal decreased by a factor of four. However, we made the surprising discovery that the noise on the ionic conduction signal decreased by about a factor of ten when using the smaller detector cell 122. Thus, the signal-to-noise ratio of the smaller detector cell 122 is better by more than a factor of two. Besides permitting a reduction in the flow of hydrogen, the smaller diameter more than doubles the signal-to-noise ratio of photo-ionization detector 12.

We believe that further improvement in signal-to-noise ratio may be obtained by changing the diameter D. Indeed, it appears that an optimum diameter D may be found for a given gas flow capable of giving even better signal-to-noise ratios than we have attained thus far. The existence of such an optimum diameter should be considered to fall within the scope of the invention.

Referring again to FIGS. 2-6 and 16, an analysis processor, shown generally at 136, identifies specific compounds on the basis of their arrival times at photo-ionization detector 12 and flame-ionization detector 14, and the amplitudes of the detection signals produced thereby. The detected signals from photo-ionization detector 12 and flame-ionization detector 14 (not shown in the presently referenced figures) are applied on lines 138 and 140, respectively, to a candidate timer 142. A peak library 144 contains data on the expected times that specific gas components should elute and be detected. Candidate timer 142 compares the time of reception of the individual peaks with those predicted by the peak library to identify candidate gas components from the two detectors.

A candidate comparison device 146 attempts to cross-match candidates inferred by the arrival times of peaks from the two detectors. For gas components expected to produce outputs from both photo-ionization detector 12 and flame-ionization detector 14, a candidate must be present in the lists produced from both detectors. If such a candidate is found on the candidate list generated from one of the detectors and is not found on the other, then the unmatched peak is discarded. Some gas components are expected to be detected by one detector and not by the other. In this case, candidate comparison device 146 does not discard an unmatched candidate.

As previously noted, the sample volumes giving rise to the detection signals contains identical gas components. Thus, each detector is exposed to identical similar quantities of each gas component eluting from its respective elution column. A knowledge of the sensitivities of each detector to individual candidate gasses permits calculating the actual concentration of a candidate gas in the sample from the amplitude of the detector output signal. If the concentration of a candidate gas detected by one detector is not equal to that detected by the other detector, after correction for detector sensitivity, then one or the other, or both, of the peaks giving rise to the selection of a candidate is produced by one or more gasses other than the candidate gas. The mismatched candidate may be discarded.

Instead of discarding a mismatched candidate, the signal responses may be processed further to attempt to identify one of the gasses which may have produced the false candidate. In one embodiment, the smaller detector signal is assumed to be produced by an known gas. The smaller signal is subtracted from the larger detector signal to produce a single reduced candidate. Then, an attempt is made to identify the single reduced candidate.

Unmatched candidates are not necessarily discarded. Since the responses of the two detectors differ for a particular gas, one detector may produce an output for a gas while the other remains unresponsive. These differences in response are known and may be used to identify a candidate gas from a single detector output. Indeed, the absence of an output from the second detector may be a criterion for identification.

A detector response library 148 contains data on the sensitivities of photo-ionization detector 12 and flame-ionization detector 14 to the gas components in peak library 144. This data is applied to a concentration calculator 150 wherein the concentrations attributable to each candidate, as tentatively identified from the output of each detector are calculated. If the concentrations calculated for a particular candidate do not match, then the candidate is false and is further processed as noted above, or discarded in a final screen 152. The candidates which pass final screen 152 make up a final list of detected gasses whose detection times and amplitudes are consistent with both the library data in peak library 144 and detector response library 148.

It is known that the elution times of gas components changes with temperature. In the prior art, this problem is dealt with by maintaining the entire instrument at a constant temperature in an electrically heated container. This is not a desired solution in a person-portable equipment wherein minimum electric consumption is desired. We have discovered, however, that the relationships between elution time and temperature can be characterized in a simple manner for candidate gasses. This data is contained in a temperature corrector library 154 and applied to peak library 144 for correction of predicted arrival times of the candidate list of compounds on the basis of a measured average column temperature, experienced by each of the sample components to be identified from the candidate list. This procedure compensates for temperature drift that may occur during analysis.

Different elution columns of the same type have variations in retention times for the same gas components. One way to develop temperature correction data for temperature corrector library 154 includes measuring the retention times of each elution column for each gas component, over the range of environmental temperatures. This would entail as many as hundreds of measurements for each instrument produced. This is not considered economic in a commercial instrument. Fortunately, we have discovered a way of characterizing the data from elution columns which permits temperature correction data to be developed and applied using only a few measurements of a limited number of gas components.

Figure 17:
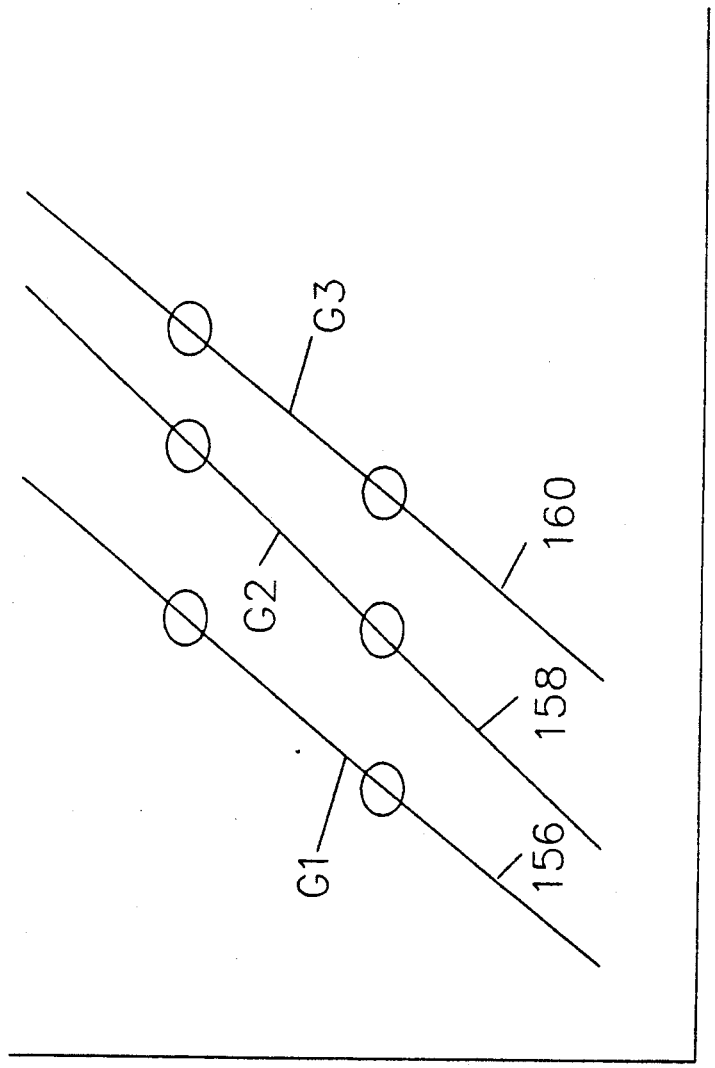
FIG. 17 is a set of curves showing mean values characterizing the temperature response of elution columns to three different gasses.

Referring now to FIG. 17, the natural logarithm of the retention time of gas components G1, G2 and G3 are plotted against the inverse of temperature. A large set of measurements for a gas component G1 at a large number of temperatures in a large number of a particular column are taken to define a mean value for the temperature response of the gas-component and column-type pair. This mean value is indicated by a straight line 156. Straight line 156 can be characterized by its slope and its intercept. Similar measurements for gas components G2 and G3 give rise to mean values indicated by straight lines 158 and 160, also capable of being characterized by their slopes and intercepts. The slopes are not necessarily parallel.

We have discovered that a particular column gives elution times that usually do not lie on the mean-value lines. Instead, a particular column tends to retain the same slopes and to shift all values a small amount either left or right in the figure. The shift can be characterized by a small change in Y-axis intercept required to displace the mean-value lines 156, 158 and 160, plus all others, into coincidence with the measured values. Thus, to obtain a calibration value for a particular column when manufacturing an instrument, a few measurements of a few gas components at a few temperatures is sufficient to define a single value for a Y-axis intercept shift which may later be applied for correcting to all values of elution time for all gasses in that elution column. In this way, a practical technique is available for calibrating an instrument which does not require the large number of measurements that would otherwise be required. Measured values for three gasses G1, G2 and G3, each at two temperatures are shown as points falling within ellipses for exemplifying the types of measurements. The ellipses should contain virtually all expected measured data points over the range of variability of different elution columns.

The foregoing illustrates how two elution columns having different types of coatings feeding gas to two detectors, also of different types, gives four dimensions (two times and two amplitudes) to aid in identification of unknown gas components. Additional dimensions could be provided Referring to FIG. 1, instead of always feeding the output of first elution column 34 to photo-ionization detector 12 and the output to second elution column 40 to flame-ionization detector 14, a two-step measurement procedure could be employed in which, initially, the described connections are made to produce two sets of detection signals, then, a further gas sample is driven through first and second elution columns 34 and 40, but their outputs are switched by valve system 26, with the output of first elution column 34 being connected to flame-ionization detector 14 and the output of second elution column 40 being connected to photo-ionization detector 12. Alternatively, two or more additional elution columns could be provided. The additional elution columns could contain coatings different from those in first and second elution columns 34 and 40. The additional elution columns could be operated simultaneously with first and second elution columns 34 and 40 using a further pair of detectors or sequentially with first and second elution columns 34 and 40 feeding photo-ionization detector 12 and flame-ionization detector 14.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What we claim is:

1. A gas analyzer comprising:
   a first chromatographic column of a type effective for selectively retarding passage of at least a first gas component therethrough for a first time period;
   a first gas detector of a first type;
   means for fluidly connecting said first chromatographic column to an inlet of said first gas detector;
   a second chromatographic column of a type effective for selectively retarding a passage of said at least a first gas component therethrough for a second time period;
   said first and second time periods being different;
   a second gas detector of a second type different from said first type;
   means for fluidly connecting said second chromatographic column to an inlet of said second gas detector;
   means for passing predetermined sample volumes of a carrier gas which may contain some of said at least first gas component through said first and second chromatographic columns;
   said first and second gas detectors having different first and second amplitude responses to said at least a first gas component; and
   means for sending and applying signals indicative of said first and second time periods and said first and second amplitude responses to an identification means of said apparatus; said identification means to which said first and second time periods and said first and second amplitude responses are applied being effective to compare the respective applied time periods and amplitude responses with library data of time periods and amplitude responses of specific gas components and thereby identify said at least a first gas component.

2. A gas analyzer according to claim 1 wherein said identification means includes a:
   means for producing a first candidate list of gas components from said first gas detector;
   means for producing a second candidate list of gas components from said second gas detector;
   means for discarding from said first and second candidate lists gas components not found on both said first and second candidate lists to form a final candidate list containing gas components found on both said first and second candidate lists;
   means for calculating a first concentration of said at lest a first gas component based on said first amplitude response of a gas component on said final candidate list;
   means for calculating a second concentration of said at lest a first gas component based on said second amplitude response of a gas component on said final candidate list; and
   said identification means being effective to identify said at least a first gas component when said first and second gas concentrations are substantially equal.

3. A method for analyzing a gas comprising:
   providing an apparatus having a first chromatographic column, a second chromatographic column, a first gas detector of a first type, a second gas detector of a type different from said first type, and gas identification means;
   passing a first predetermined sample volume of said gas through said first chromatographic column, said first column being of a type effective for selectively retarding passage of at least a first gas component therethrough for a first time period;
   passing an effluent of said first chromatographic column to said first gas detector of a first type;
   passing a second predetermined sample volume of said gas through said second chromatographic column, said second column being of a type effective for selectively retarding a passage of said at least a first gas component therethrough for a second time period;
   said first and second time periods being different;
   passing an effluent of said second chromatographic column through said second gas detector of a second type different from said first type;
   said first and second gas detectors having different first and second amplitude responses to said at least a first gas component; sending signals indicative of said first and second time periods and of said first and second amplitude responses to said identification means; and
   identifying said at least a first gas component by comparing said first and second time periods and said first and second amplitude responses with a library data of respective time periods and amplitude responses of gas components of said identification means to indicate a presence of said at least a first gas component.

4. A gas detector and analyzer comprising:
   a first gas detector of a first type;
   a second gas detector of a second type different from said first type;

means for sequentially passing a flow of a sample gas through said first and second gas detectors;

means in said first and second gas detectors for producing first and second electronic signals in response to at least a first gas component passing therethrough;

means for indicating a presence of said at least a first gas component in response to either one or both of said electronic signals;

a first chromatographic column of a type effective for selectively retarding passage of said at least a first gas component therethrough for a first time period;

means for fluidly connecting said first chromatographic column to an inlet of said first gas detector;

a second chromatographic column of a type effective for selectively retarding a passage of said at least a first gas component therethrough for a second time period;

said first and second time periods being different;

means for fluidly connecting said second chromatographic column to an inlet of said second gas detector;

means for passing predetermined sample volumes of a carrier gas which may contain some of said at least a first gas component through said first and second chromatographic columns;

said first and second gas detectors having different first and second amplitude responses to said at least a first gas component; and means for sending and applying signals indicative of said first and second time periods and said first and second amplitude responses to an identification means of said apparatus; said identification means to which said first and second time periods and said first and second amplitude responses are applied being effective to compare the respective applied time periods and amplitude responses with library data of time periods and amplitude responses of specific gas components and thereby identify said at least a first gas component.

5. Apparatus according to claim 4 wherein one of said first and second detector types is a flame ionization detector.

6. Apparatus according to claim 5 wherein the other of said first and second detector types is a photo-ionization detector.

* * * * *